US00PP24354P2

(12) United States Plant Patent
Korlipara

(10) Patent No.: US PP24,354 P2
(45) Date of Patent: Mar. 25, 2014

(54) ***ECHINACEA* PLANT NAMED 'SECRET AFFAIR'**

(50) Latin Name: ***Echinacea* spp.**
Varietal Denomination: Secret Affair

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 56 days.

(21) Appl. No.: 13/573,346

(22) Filed: Sep. 11, 2012

(51) Int. Cl.
*A01H 5/00* (2006.01)

(52) U.S. Cl.
CPC ..... *A01H 5/00* (2013.01)
USPC ..... Plt./428

(58) Field of Classification Search
CPC ..... A01H 5/00; A01H 4/00; A01H 1/00; A01H 1/04; A01H 1/06
USPC ..... Plt./428
See application file for complete search history.

*Primary Examiner* — Annette Para
(74) *Attorney, Agent, or Firm* — Klarquist Sparkman, LLP

(57) ABSTRACT

A new and distinct *Echinacea* plant named 'Secret Affair' characterized by enlarged disc florets forming an anemone-type inflorescence, deep pink disc and ray florets, a medium sized, mounding habit with good stem count and branching, and excellent vigor.

1 Drawing Sheet

Botanical denomination: *Echinacea* spp.
Variety designation: 'Secret Affair'.

BACKGROUND OF THE INVENTION

The present invention relates to a new and distinct cultivar of *Echinacea* and given the cultivar name 'Secret Affair'. *Echinacea* is in the family Asteraceae. This new cultivar is a fifth generation seeding originating from a planned breeding program using *Echinacea paradoxa* (an unpatented plant) as the seed parent in the original cross and *Echinacea purpurea* 'Ruby Giant' (an unpatented plant) as the pollen parent. The exact parents of this selection are unknown, unnamed, proprietary plants.

Compared to *Echinacea* 'Gum Drop' (U.S. Plant Pat. No. 22,132), the new cultivar is much shorter and has darker ray florets.

Compared to *Echinacea* 'Razzmatazz' (an unpatented plant) the new cultivar has larger, darker pink flowers and a much smaller habit.

This new *Echinacea* cultivar is distinguished by:

1. enlarged disc florets forming an anemone-type inflorescence,
2. deep pink disc and ray florets,
3. a medium sized, mounding habit with good stem count and branching, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows the inflorescences of *Echinacea* 'Secret Affair' on a one-and-a-half-year-old plant growing in the garden in full sun in late August in Canby, Oreg.

DETAILED PLANT DESCRIPTION

The following is a detailed description of the new *Echinacea* cultivar based on observations of a one-and-a-half-year-old plant growing in the garden in full sun in late July in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type.*—Herbaceous perennial.
*Hardiness.*—USDA Zones 4 to 9.
*Size.*—Grows to about 42 cm wide and 56 cm tall to top of inflorescences.
*Form.*—Basal clump, with about 25 stems from the crown.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 1 to 4 inflorescences per stem.
*Size.*—To 53 cm tall to a terminal inflorescence and 6 mm wide at base.
*Internode length.*—2 cm to 5 cm.
*Surface texture.*—Strigose.
*Color.*—Yellow Green 146C.

Leaf (basal):

*Type.*—Simple.
*Shape.*—Lanceolate.
*Arrangement.*—Basal.

*Blade size.*—Grows to 13 cm long and 5.5 cm wide.
*Margins.*—Coarsely serrate.
*Apex.*—Acute.
*Base.*—Attenuate.
*Surface texture.*—Strigose on both sides.
*Venation.*—Pinnate, with 3 main veins, veins Yellow Green 146C.
*Color.*—Topside Green 137A bottom side closest to Yellow Green 147B.
*Petiole description.*—Grows to 24 cm long and 5 mm wide, strigose, Yellow Green 146C lightly tinted Greyed Purple 187A, strongly tinted 187A at base.

Leaf (stem):
*Type.*—Simple.
*Shape.*—Lanceolate.
*Arrangement.*—Alternate.
*Blade size.*—Grows to 8 cm long and 4 cm wide.
*Margins.*—Coarsely serrate.
*Apex.*—Acute to acuminate.
*Base.*—Attenuate.
*Surface texture.*—Strigose on both sides.
*Venation.*—Pinnate, with 3 main veins from the base, veins Yellow Green 146C.
*Color.*—Topside Yellow Green 137A, bottom side closest to Yellow Green 147B.
*Petiole description.*—On all but upper leaves, clasping, grows to 3.5 cm long and 6 mm wide above the clasp, strigose, both sides Yellow Green 147D in the middle, topside leaf sides Yellow Green 137A with base tinted Greyed Purple 187A, bottom side leaf side closest to Yellow Green 147B.

Inflorescence:
*Type.*—Composite on terminal stalked heads.
*Number of flowering stems from the ground.*—About 25.
*Flowering stem.*—Grows to 53 cm tall from the base of the plant to the terminal inflorescence and can grow to 18 cm long from the top stem leaf to the base of an inflorescence; branched with 1 to 4 inflorescences per stem; diameter growing to 8 mm wide near the inflorescence; strigose; Yellow Green 146C.
*Size.*—Grows to 9.5 cm wide and 6 cm deep as disc enlarges.
*Form.*—Ray florets held slightly reflexed, mature disc is conic.
*Immature inflorescence.*—Grows to 2.5 cm wide and 2 cm deep, ray florets held at a 60 degree angle from the horizontal and rolled up so only the back color shows, florets Red Purple 64A with tips Yellow Green 145D.
*Ray florets.*—About 20 in number, grow to 47 mm long and 8 mm wide, oblanceolate with the tip two to three-toothed (each acute), entire margins, base attenuate, glabrous on both sides; topside closest to Red Purple 64A, bottom side Purple N77B; each with 1 pistil, ovary 3 mm long, White 155A, style 6 mm long, Greyed Purple 187B, 2-branched stigma spreading, Greyed Purple 187A.
*Disc.*—Flat becoming globe-like, growing to 45 mm deep and 60 mm wide with maturity, Red Purple 71A.
*Disc florets.*—About 200 in number, each with 1 pistil and 4 stamen, grow to 24 mm long and 5 mm to 9 mm wide, each with one persistent, very stiff linear bract (12 mm long with the top 1 mm colored Greyed Purple 187A, blending to next 2 mm Orange 26A then 5 mm Yellow Green 144A in middle, then Yellow Green 145D on bottom); corollas 20 mm long and 5 mm to 9 mm wide, tubular at base for 3 mm (N77C) then spreads out like a fan with two to four teeth or lobes, teeth usually 2 mm deep and 1.5 mm wide, lobes to 10 mm long 1.5 mm wide, acute tip, glabrous on both sides, entire margins, topside Red Purple 71A, bottom side Purple N77B; pistil 10 mm long, ovary 4 mm long, White 155A, style 6 mm long Greyed Purple 187B, 2-branched stigma spreading, Greyed Purple 187A; stamen 4 mm long, filaments 4 mm long, threadlike, Yellow Green 145D, anthers none, pollen none.
*Phyllaries.*—In 4 leafy series, area grows to 28 mm wide and 10 mm deep, lobes lanceolate in shape, reflexed, grow to 10 mm long and 2.5 mm wide, Green 137A, margins strigose, tip acute, strigose on both sides.
*Receptacle.*—Grows to 14 mm wide and 14 mm deep, White NN155B.
*Bloom period.*—July through October in Canby, Oreg.
*Fragrance.*—Light.
*Lastingness.*—Each inflorescence lasts about two weeks in Canby, Oreg.
*Seeds.*—Not seen.
*Fertility.*—Poor.

Disease and pests: No pests or diseases have been observed on plants grown under commercial conditions in Canby, Oreg. No resistances are known.

I claim:

1. A new and distinct *Echinacea* plant as herein illustrated and described.

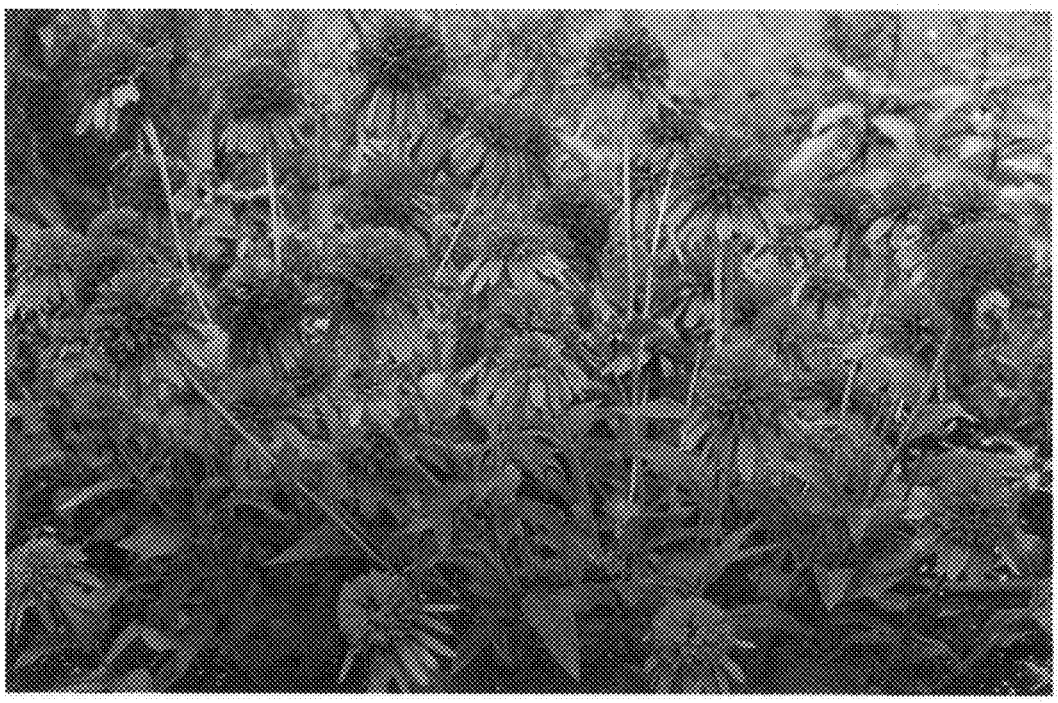

* * * * *